(12) United States Patent
Rogers-Evans

(10) Patent No.: US 7,262,307 B2
(45) Date of Patent: Aug. 28, 2007

(54) 1'-BENZYL-3-BROMO-[1,3']BIPYRROLI-DINYL-2-ONE

(75) Inventor: Mark Rogers-Evans, Binningen (CH)

(73) Assignee: Basilea Pharmaceutica AG (CH)

( * ) Notice: Subject to any disclaimer, the term of this patent is extended or adjusted under 35 U.S.C. 154(b) by 559 days.

(21) Appl. No.: 10/916,954

(22) Filed: Aug. 12, 2004

(65) Prior Publication Data

US 2005/0070722 A1 Mar. 31, 2005

Related U.S. Application Data

(62) Division of application No. 10/344,903, filed on Feb. 14, 2003, now Pat. No. 6,828,442.

(30) Foreign Application Priority Data

Aug. 14, 2000 (EP) .................................. 00117525
Aug. 6, 2001 (WO) ...................... PCT/EP01/09059

(51) Int. Cl.
*C07D 207/04* (2006.01)

(52) U.S. Cl. ...................................................... 548/518
(58) Field of Classification Search ................ 548/518
See application file for complete search history.

(56) References Cited

U.S. PATENT DOCUMENTS 5,804,577 A  9/1998  Hebeisen et al.
5,981,519 A  11/1999  Angehrn et al.

FOREIGN PATENT DOCUMENTS

EP  849 269  6/1998

OTHER PUBLICATIONS

Jacques Maddaluno et al., "Handy Access to Chiral N, N'-Disubstituted 3-Aminopyrrolidines," Tetrahedron: Asymmetry, 1992, vol. 3, No. 10, p. 1239-1242.

*Primary Examiner*—Golam M. M. Shameem

(57) ABSTRACT

The compound (R)-(1'-benzyl-3-bromo-[1,3']bipyrrolidinyl-2-one) which is an intermediate for antibacterial vinylpyr-rolidinone-cephalosporin derivatives.

1 Claim, No Drawings

1'-BENZYL-3-BROMO-[1,3']BIPYRROLI-DINYL-2-ONE

CROSS REFERENCE TO RELATED APPLICATION

This application is a divisional application of Ser. No. 10/344,903 filed Feb. 14, 2003, now U.S. Pat. No. 6,828,442.

The invention relates to a new process for the preparation of (1'-tert-butoxycarbonyl-2-oxo-[1,3']-bipyrrolidinyl-3-(R,S)-yl)-triphenyl-phosphonium halogenide compounds of formula I

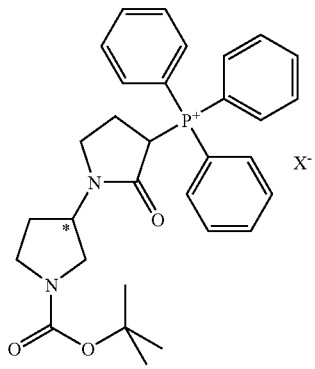

I wherein * signifies an asymmetric center with an (R) or (S) configuration and X represents chlorine, bromine or iodine.

The compounds of formula I are known from EP-A 0 849 269 and can be obtained through multiple-step synthesis of the corresponding allyloxycarbonyl (ALLOC) protected [1,3']bipyrrolidinyl-2-oxo derivative by removal of the allyloxycarbonyl protecting group and protection reaction with a tert-butoxycarbonyl moiety to yield tert-butoxycarbonyl (t-BOC) protected [1,3']bipyrrolidinyl-2-oxo compounds of formula I.

It has now been found that the compounds of formula I can be manufactured in an improved and shortened way by the process of the present invention. The new process for the preparation of (1'-tert-butoxycarbonyl-2-oxo-[1,3']-bipyrrolidinyl-3-(R,S)-yl)-triphenyl-phosphonium halogenide compounds of formula I

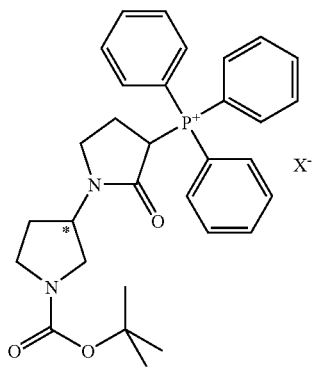

I wherein * signifies an asymmetric center with an (R) or (S) configuration and X represents chlorine, bromine or iodine;

comprises step 1) coupling N-benzyl-3-pyrrolidinamine of formula II

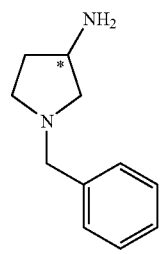

II wherein * is as defined above with a compound of formula X(CH$_2$)$_2$CH(X)COX wherein X is independently of each other chlorine, bromine or iodine; and subsequent cyclization in the presence of a base to obtain a compound of formula III

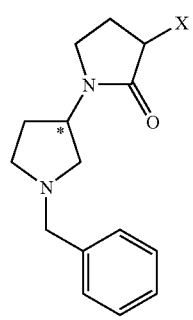

III wherein * and X are as defined above;

step 2) reacting the compound of formula III with triphenylphosphine to obtain the phosphonium salt of formula IV

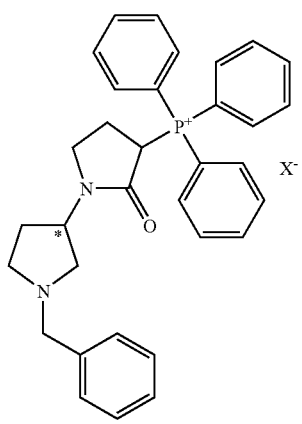

IV wherein * and X are as defined above; and step 3) reacting the phosphonium salt of formula IV with di-tert.-butyl-dicarbonate under hydrogenation conditions to obtain the compounds of formula I.

Surprisingly, it has been found that the N-benzyl-3-pyrrolidinamine of formula II undergoes the reaction sequence described above to yield the compounds of formula I, despite the expected instability of intermediate III. The corresponding t-Boc and Alloc protected derivatives of starting material of formula II are not available through the described process In the structural formulae of the compounds given throughout this application, a wedged bond (━)

indicates a substituent which is above the plane of the paper.

In the structural formulae of the compounds given throughout this application, a dotted bond (·····)

indicates a substituent which is below the plane of the paper.

The compounds of the present process invention exhibit stereoisomerism and can be any stereoisomer. The compounds of the present process invention having one asymmetric carbon atom may be obtained as racemic mixtures of stereoisomers which can be resolved, at the appropriate steps in the process of this invention by methods well known in the art to obtain a given stereoisomer or pure enantiomer having a desired stereoconfiguration. Alternatively, the desired isomers may be directly synthesized by methods known in the art.

The asymmetric carbon atom in the compound of the present invention is denoted as "*". The stereoconfiguration of the asymmetric carbon atom denoted as "*" can be designated according to the particular stereoisomer it represents. Compounds of the present invention include those compounds wherein the carbon atom denoted as "*" have the S,R or R,S-configuration, preferably the R-configuration.

The term halogen stands for chlorine, bromine and iodine, more preferred chlorine or bromine, most preferred halogen is bromine.

The compounds of the present invention are prepared as shown in the reaction scheme 1.

Reaction scheme 1:

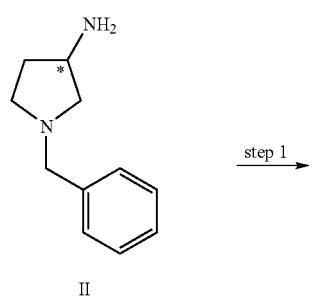

II wherein * and X are as defined above.

In the 1$^{st}$ step of the reaction the compound of formula II is coupled with 1-4 equivalents, preferably 1-2 equivalents of X(CH$_2$)$_2$CH(X)COX wherein X is independently of each other chlorine or bromine or iodine, preferably bromine (preparation see below) in the presence of bases such as Na$_3$PO$_4$, K$_2$CO$_3$, Na$_2$CO$_3$, KOH or NaOH, preferably Na$_3$PO$_4$ and an appropriate solvent. Appropriate solvents are polar aprotic solvents such as acetonitrile (CH$_3$CN), dimethylsulfoxide (DMSO), dimethylacetamide or N,N-dimethylformamide (DMF), preferably CH$_3$CN. The reaction is carried out at a reaction temperature between about −20° C. and about 30° C., preferably at a reaction temperature between about −10° C. and about 10° C. Subsequently, a cyclization reaction is carried out with the intermediate coupling product to obtain compounds of formula III. The cyclization reaction is carried out in the presence of 1-3 equivalents, preferably 2-2.5 equivalents of a base, such as $K_2CO_3$, $Na_2CO_3$, KOH or NaOH, preferably NaOH in aqueous solution, at a reaction temperature between about −10° C. and about 50° C., preferably between about 10° C. and about 30° C.

Compounds of formula $X(CH_2)_2CH(X)COX$ wherein X is independently of each other chlorine or bromine or iodine are commercially available or are synthesized according to methods known from textbooks. For example the compound of formula $X(CH_2)_2CH(X)COX$ wherein X is chlorine is prepared according to Mathew, K. K. et al. Indian J. Chem., Sect. B (1981), 20B(4), 340-2. The compound of formula $X(CH_2)_2CH(X)COX$ wherein X is bromine is prepared according to Marinelli, E. R. et al. Tetrahedron (1996), 52(34), 11177-11214. The compound of formula $X(CH_2)_2CH(X)COX$ wherein X is iodine can be obtained by reacting the tribromide (X=Br) with NaI in $CH_3CN$.

In a preferred embodiment of the invention the compound of formula IIIa

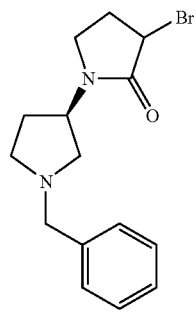

IIIa is formed according to the above described 1$^{st}$ step of the reaction. The compound of formula IIIa is new and therefore part of the present invention.

In the 2$^{nd}$ step of the process the compound of formula III is reacted with 1-5 equivalents, preferably 2-4 equivalents of triphenylphosphine to obtain the phosphonium salt of formula IV. The reaction is carried out in an aromatic solvent such as toluene, o-xylene, m-xylene, p-xylene or benzene, preferably toluene at a reaction temperature between about 20° C. and about 180° C., preferably between about 80° C. and about 140° C.

In a preferred embodiment of the invention the compound of formula IVa

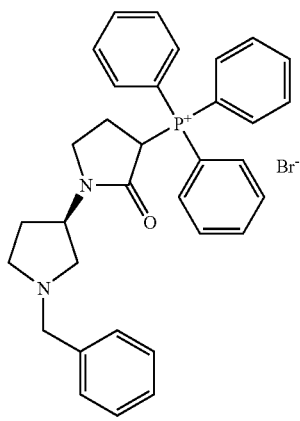

IVa is formed according to the above described 2$^{nd}$ step of the reaction. The compound of formula IVa is new and therefore part of the present invention.

In the 3$^{rd}$ step of the process the phosphonium salt of formula IV is reacted with 1-5 equivalents, preferably 2-4 equivalents of di-tert.-butyl-dicarbonate (commercially available from Fluka) under hydrogenation conditions in the presence of a catalyst such as Pd/C (commercially available from Degussa) preferably with 10% Pd on activated carbon, to obtain compounds of formula I. The reaction is carried out in an alcoholic solvent such as methanol, ethanol or isopropanol, preferably in methanol at a reaction temperature between about 10° C. and about 100° C., preferably between about 40° C. and about 80° C.

In a preferred embodiment of the invention steps 1-3 are carried out for compounds wherein * signifies an asymmetric center with (R) configuration and X is chlorine or bromine, preferably bromine.

Compounds of formula II, used as starting material in the present process is prepared according reaction steps a→b→c as shown in reaction scheme 2. The preparation of the compound of formula II is also part of the present invention.

Reaction scheme 2:

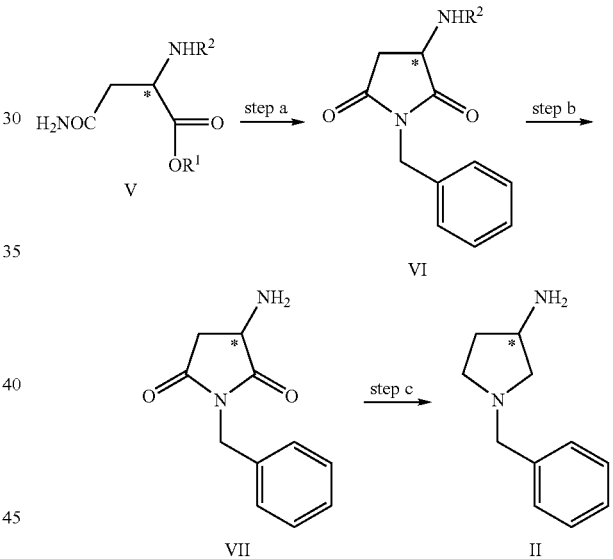

wherein R$^1$ is alkyl, R$^2$ is an amino protecting group and * is as defined above.

The terms which have already been mentioned and will be mentioned in the description of the invention are defined as follows:

The term "alkyl" as used herein denotes an optionally substituted straight or branched chain hydrocarbon residue containing 1 to 12 carbon atoms, such as methyl, ethyl, propyl, isopropyl, n-butyl, isobutyl, tert.-butyl, pentyl, hexyl, heptyl, octyl, nonyl, decyl, undecyl, dodecyl and its isomers.

Alkyl in R$^1$ is preferably unsubstituted straight or branched chain hydrocarbon residue containing 1 to 4 carbon atoms, more preferred methyl or ethyl, and most preferred methyl.

The term "amino protecting group" as used herein refers to groups such as those employed in peptide chemistry, such as an allyloxycarbonyl group (ALLOC), a lower alkoxycarbonyl group such as tert-butoxycarbonyl (t-BOC) and the like, a substituted lower alkoxycarbonyl group such as trichloroethoxycarbonyl, an optionally substituted aryloxycarbonyl group for example p-nitrobenzyloxycarbonyl or benzyloxycarbonyl (Z), an arylalkyl group such as triphenylmethyl (trityl), benzhydryl or benzyl, an alkanoyl group such as formyl, acetyl or benzoyl, a halogen-alkanoyl group such as trifluoroacetyl, or a silyl protective group such as the tert-butyldimethylsilyl group.

Preferred amino protecting groups are benzyloxycarbonyl, tert-butoxycarbonyl or allyloxycarbonyl.

An especially preferred amino protecting for $R^2$ is the benzyloxycarbonyl group.

The term "lower alkoxy" signifies an alkyl group as defined above which is bonded via an oxygen atom. Examples are methoxy, ethoxy, propyloxy, butoxy, tert.butoxy and the like.

The term "aryl" as used herein denotes an optionally substituted phenyl group (Ph) in which one or more aryl hydrogen atoms can be substituted by one or more phenyl groups, alkyl groups, lower alkoxy groups, halogenated alkyl groups, halogen atoms or nitro. Examples are phenyl, o-tolyl, m-tolyl, p-tolyl, o-methoxyphenyl, m-methoxyphenyl, p-methoxyphenyl, o-trifluoromethylphenyl, m-trifluoromethylphenyl, p-trifluoromethylphenyl, o-trichloromethylphenyl, m-trichloromethylphenyl, p-trichloromethylphenyl, p-fluorophenyl p-chlorophenyl, p-bromophenyl, p-nitrophenyl.

The term "aryloxy" signifies an aryl group as defined above which is bonded via an oxygen atom. Examples are phenyloxy, benzyloxy and the like.

The term "lower alkoxycarbonyl" denotes lower alkoxy residues as defined, attached to a carbonyl group (—C(=O)). Examples are methoxycarbonyl, ethoxycarbonyl, propoxycarbonyl, tert-butoxycarbonyl and the like.

The term "aryloxycarbonyl" denotes aryloxy residues as defined, attached to carbonyl group (—C(=O)). Examples are phenyloxycarbonyl and benzyloxycarbonyl.

The term "arylalkyl" as used herein denotes a hydrocarbon group in which one or more alkyl hydrogen atoms are substituted by an aryl group as defined. Examples are trityl, benzhydryl or benzyl.

The term "hydroxy protecting group" as used herein denotes an alkyl group, a cycloalkyl group or an arylalkyl group. A preferred hydroxy protecting group is an arylalkyl group, especially preferred is a triphenylmethyl (trityl) group.

The term "carboxylic acid protecting group" includes protecting groups which are usually used to replace a proton of the carboxyl group. Examples of such groups are described in Green T. Protective Groups in Organic Synthesis, Chapter 5, John Wiley and Sons, Inc. (1981), pp. 152-192. Examples of such protecting groups are: benzhydryl, tert.-butyl, p-nitrobenzyl, p-methoxybenzyl, methoxymethyl and the like. Benzhydryl is a preferred carboxylic acid protecting group.

The term "cycloalkyl" as used herein denotes a 3-6 membered saturated carbocyclic moiety, e.g. cyclopropyl, cyclobutyl, cyclopentyl or cyclohexyl, preferably cydohexyl.

In step (a) of the reaction the asparagine derivatives of formula V (preparation see below) is treated with 0.5-2.0 equivalents, preferably 1.0-1.5 equivalents of a base such as NaH, NaOH or KOH, preferably with NaH, in an appropriate solvent to obtain the cyclic intermediate of formula A

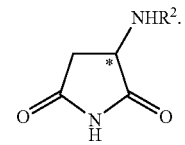

wherein * and $R^2$ are as defined above.

Appropriate solvents for the cyclization reaction are ethers such as tetrahydrofuran, diethyl ether, dioxane or a mixture of the mentioned solvents, preferably tetrahydrofuran. Then, in a preferred embodiment of the invention, the intermediate of formula A is reacted with commercially available benzyl bromide in the presence of an appropriate solvent to obtain the 3-amino protected benzyl-2,5-dioxopyrrolidine of formula VI. Appropriate solvents are polar aprotic solvents such as dimethylsulfoxide (DMSO), dimethylacetamide or N,N-dimethylformamide (DMF), preferably DMF. The reaction is carried out at a temperature between about 0° C. and about 50° C., preferably between about 10° C. and about 40° C.

In another embodiment of the invention the intermediate of formula A is reacted with commercially available p-methoxybenzylbromide, 3,4-dimethoxybenzylbromide, trityl chloride, methoxy methyl chloride or allyl bromide under above-described reaction conditions or alternatively according to methods known from textbooks on organic chemistry (e.g. J. March (1992), "Advanced Organic Chemistry: Reactions, Mechanisms, and Structure", $4^{th}$ ed. John Wiley & Sons) to obtain the corresponding 1-N-substituted 3-amino protected-2,5-dioxo-pyrrolidine of formula VI.

The reaction of step (a) can optionally be carried via a two step procedure. First, the asparagine derivatives of formula V is treated with 0.5-2.0 equivalents, preferably 1.0-1.5 equivalents of a base such as NaH, NaOH or KOH, preferably with NaH in an appropriate solvent to obtain the cyclic compound of formula A. Appropriate solvents for this first step are ethers such as tetrahydrofuran, diethyl ether, dioxane or a mixture of the mentioned solvents, preferably tetrahydrofuran. The reaction is carried out at a temperature between about –10° C. and about 30° C., preferably starting at 0° C.; during the reaction the temperature is increased to room temperature. After the reaction, the reaction mixture is acidified to a pH in the range between 3.0 and 5.0, preferably between 3.5 and 4.5, and then the organic solvent is evaporated. Secondly, the compound of formula A is treated with a base such as NaH, NaOH or KOH, preferably with NaH in ethers such as tetrahydrofuran, diethyl ether, dioxane or a mixture of the mentioned solvents, preferably in tetrahydrofuran.

Then, in a preferred embodiment of the invention, the mixture is reacted with commercially available benzyl bromide in the presence of an appropriate solvent to obtain the 3-amino protected benzyl-2,5-dioxo-pyrrolidine of formula VI. Appropriate solvents for the reaction are polar aprotic solvents such as dimethylsulfoxide (DMSO), dimethylacetamide or N,N-dimethylformamide (DMF), preferably DMF. The reaction is carried out at a temperature between about –10° C. and about 30° C., preferably starting at 0° C.; during the reaction the reaction temperature is increased to room temperature. After the reaction, the product is worked-up in a manner known in the art for example quenched with $H_2O$ and extracted with an aromatic solvent such as toluene, o-xylene, m-xylene, p-xylene or benzene preferably toluene, dried over anhydrous magnesium sulfate, sodium sulfate, calcium chloride, preferably magnesium sulfate and finally the organic solvent is evaporated.

In another embodiment of the invention the mixture is reacted with commercially available p-methoxybenzylbromide, 3,4-dimethoxybenzylbromide, trityl chloride, methoxy methyl chloride or allyl bromide under above-described reaction conditions or alternatively according to methods known from textbooks on organic chemistry (e.g. J. March (1992), "Advanced Organic Chemistry: Reactions, Mechanisms, and Structure" $4^{th}$ ed. John Wiley & Sons) to obtain the corresponding 1-N-substituted 3-amino protected-2,5-dioxo-pyrrolidine of formula VI.

Asparagine derivatives of formula V are commercially available or can be synthesized according to methods known from textbooks on organic chemistry (e.g. J. March (1992), "Advanced Organic Chemistry: Reactions, Mechanisms, and Structure", $4^{th}$ ed. John Wiley & Sons) for example starting with D- or L-asparagine (Fluka) protection of the free amino function and subsequent esterification to obtain the corresponding asparagine derivatives of formula V.

The advantage of carrying out the reaction of step (a) via a two step procedure is that the compounds of formula VI are obtained in higher yield. The two step procedure is also a part of the present invention.

In step (b) of the process the amino protecting group ($R^2$) of the compounds of formula VI is removed under condition described below. Preferred amino protecting groups for $R^2$ are benzyloxycarbonyl, tert-butoxycarbonyl or allyloxycarbonyl, most preferred benzyloxycarbonyl. The benzyloxycarbonyl amino protecting group is for example removed under hydrogenation conditions in the presence of a catalyst such as Pd/C (commercially available from Degussa) preferably with 10% Pd on activated carbon. The deprotection reactions are carried out in the presence of acetic acid, trifluoroacetic acid, ethanolic HCl, methanesulphonic acid or fluorosuphonic acid to obtain the corresponding amino salt of formula VII which is more stable than the free base and therefore can be stored without degradation. In a preferred embodiment acetic acid is used to prepare the acetic acid salt of formula VII. The reaction is carried out at a temperature between about 10° C. and about 50° C., preferably between about 20° C. and about 40° C.

Depending on the amino protecting groups the deprotection is carried out as follows:

The amino protecting groups maybe cleaved off by acid hydrolysis (e.g. the tert-butoxycarbonyl or trityl group), e.g. aqueous formic acid, trifluoroacetic acid or by basic hydrolysis (e.g. the trifluoroacetyl group). Further protecting groups maybe cleaved off by hydrazinolysis (e.g. the phthalimido group). The allyloxycarbonyl group may be cleaved off by Pd catalysed transfer to nucleophiles. The chloroacetyl, bromoacetyl and iodoacetyl groups are cleaved off by treatment with thiourea.

Amino protecting groups which are cleavable by acid hydrolysis are preferably removed with the aid of a lower alkanecarboxylic acid which may be halogenated. In particular, formic acid or trifluoroacetic acid is used. The reaction is carried out in the acid or in the presence of a co-solvent such as a halogenated lower alkane, e.g. methylene chloride. The acid hydrolysis is generally carried out at room temperature, although it can be carried out at a slightly higher or slightly lower temperature (e.g. a temperature in the range of about −30° C. to 40° C.). Protecting groups which are cleavable under basic conditions are generally hydrolyzed with dilute aqueous caustic alkali at 0° C. to 30° C. The chloroacetyl, bromoacetyl and iodoacetyl protecting groups can be cleaved off using thiourea in acidic, neutral or alkaline medium at about 0° C. to 30° C.

In step (c) of the process the amino salt compound of formula VII is treated with a base such as NaOH, KOH, $Na_2CO_3$ or $K_2CO_3$ preferably with NaOH in aqueous solution to adjust the pH in the ranges from 7.0 to 9.0, preferably in the range from 7.5 to 8.5 in the presence of a halogenated hydrocarbon such as monochloromethane or dichloromethane, preferably dichloromethane, to remove the acid and to obtain the intermediate acid free compound of formula VII. The intermediate is then worked-up by extraction with a halogenated hydrocarbon such as monochloromethane or dichloromethane, preferably dichloromethane and then the organic solvent is evaporated. Subsequently, the acid free derivative of formula VII is reduced with a reducing agent such as Vitride®, $NaBH_4$, $LiBH_4$, $LiAlH_4$, $BH_3$.THF, preferably with Vitride®, to obtain the amino pyrrolidine of formula II. The reducing agents are commercially available from Aldrich or Fluka. The reaction is carried out in an aromatic solvent such as toluene, o-xylene, m-xylene, p-xylene or benzene, preferably with toluene at a reaction temperature between about −10° C. and about 100° C., preferably starting at 0° C.; during the reaction the temperature is increased to 80° C. Then, the mixture is cooled to a temperature between about −20° C. and about 20° C., preferably to a temperature between about −10° C. and about 10° C. and treated with a base such as sodium hydroxide in aqueous solution.

In a preferred embodiment of the process steps a-c are carried out for compounds wherein * signifies an asymmetric center with (R) configuration and $R^1$ is methyl or ethyl, preferably methyl and $R^2$ is benzyloxycarbonyl, tert-butoxycarbonyl or allyloxycarbonyl, preferably benzyloxycarbonyl and X is chlorine or bromine, preferably bromine.

The compounds of formula I-VII are important building blocks for the production of useful products in the chemical and pharmaceutical industry. In particular they are useful for the production of antibacterial substances for example vinylpyrrolidinone-cephalosporin derivatives as described in EP-A 0 849 269. Preferably compounds of formula I-VII are useful for the preparation of compounds of formula VIII

VIII

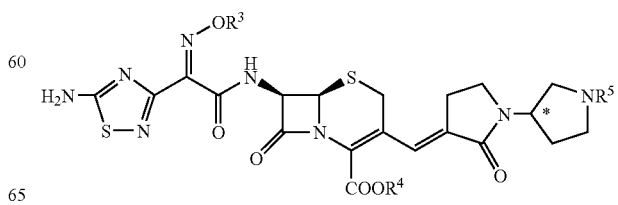

wherein R³ is a hydroxy protecting group, R⁴ is a carboxylic acid protecting group, is as defined above and R⁵ is an amino protecting group preferably a tert-butoxycarbonyl group or a group of formula B

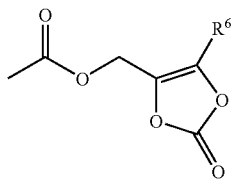

B wherein R⁶ is preferably an unsubstituted straight chain or branched alkyl group containing 1 to 4 carbon atoms, more preferred methyl, ethyl or isopropyl and most preferred methyl.

The preparation of compounds of formula VIII is described in EP-A 0 849 269.

In the following examples the abbreviations used have the following signification's.

ISP-MS ion spray positive mass spectroscopy
EI-MS electron impact mass spectroscopy
GC gas chromatography
SFC super critical fluid chromatography
NMR nuclear magnetic resonance spectroscopy
IR infrared spectroscopy
TLC thin layer chromatography
HPLC high performance liquid chromatography
HV high vacuum
FID flame ionization detector
THF tetrahydrofurane
DMF N,N-dimethylformamide
DMSO dimethylsulfoxide
TBME tert.-butyl methyl ether
TFA trifluoracetic acid
TBAHS tetrabutylammonium hydrogen sulfate
min minute(s)
h hour(s)
rt room temperature

EXAMPLE 1

Preparation of (R)-(1-benzyl-2,5-dioxo-pyrrolidin-3-yl)-carbamic acid benzyl ester 1.1 (via one step): A suspension of 1.12 g of 60% NaH in 75 ml of THF is treated with 7.50 g of Z-(D)-asparagine methyl ester (99.9% (R)-isomer) (synthesized according to J. Liq. Chromatogr. (1994), 17(13), 2759 or for example starting with D-asparagine (Fluka) and protecting the free amino function with a benzyloxycarbonyl group and subsequent esterification to the corresponding methyl ester asparagine derivative of formula I; the reactions are carried out according to textbook of organic chemistry e.g. J. March (1992), "Advanced Organic Chemistry: Reactions, Mechanisms, and Structure", 4ᵗʰ ed. John Wiley & Sons) over 5 min at rt. After 20 min, 3.57 ml of benzyl bromide (commercially available from Fluka) was added, followed by 120 ml of DMF. After 3 h, the conversion was completed (indicated by HPLC). The reaction was quenched with 150 ml H₂O and extracted three times with 120 ml of toluene. The organic layer was washed with H₂O, dried over MgSO₄, filtered and the filtrate was evaporated to dryness. The residue was triturated in 100 ml of TBME, the resultant suspension filtered and dried (35° C./10 mbar) to give 8.13 g (90%) of (R)-(1-benzyl-2,5-dioxo-pyrrolidin-3-yl)-carbamic acid benzyl ester as white crystals: m.p. 143.3-144.5° C. Optically pure material could be obtained from crystallization from CH₂Cl₂/n-hexane, 72% recovery; m.p. 145.9-146.7° C.; 99.9% (R)-isomer.

1.2.1 (via two steps; 1ˢᵗ step): A suspension of 856 mg of 60% NaH in 50 ml THF at 0° C. was treated with 5.0 g of Z-(D)-asparagine methyl ester 3 (99.9% (R)-isomer) and stirred at rt for 90 min whereupon TLC indicated complete consumption of the starting material. The reaction mixture was acidified to pH 4 with 6.0 ml of AcOH and the THF distilled away. The remaining aqueous layer was extracted three times with 20 ml of TBME and the combined organic phases washed with 20 ml of brine, dried over MgSO₄ and concentrated to give 4.66 g of a white sticky solid (105% contains ~5% w/w AcOH) of (R)-(2,5-dioxo-pyrrolidin-3-yl)-carbamic acid benzyl ester as a white sticky solid which was used directly for the second step (example 1.2.2) below. Digestion in EtOAc/n-hexane gave 3.47 g (75%) of (R)-(2, 5-dioxo-pyrrolidin-3-yl)-carbamic acid benzyl ester as white crystals, m.p. 117.2-117.8° C.

1.2.2 (via two steps; 2ⁿᵈ step): A suspension of 48.4 mg of 60% NaH in 3 ml of THF was treated with 300 mg of (R)-(2,5-dioxo-pyrrolidin-3-yl)-carbamic acid benzyl ester at 0° C. followed by 161.3 μL of benzyl bromide. After 30 min the resulting precipitate was warmed to rt and treated with 3 ml of DMF to give after 15 min a solution which was stirred for 16 h at rt then quenched with 60 ml of H₂O and extracted with 40 ml of toluene. The combined organic layers were dried over MgSO₄ and concentrated to give 409 mg (74%) of the (R)-(2,5-dioxo-pyrrolidin-3-yl)-carbamic acid benzyl ester as white crystals; m.p. 145.1-145.5° C. Overall yield for the two step process: 78%.

EXAMPLE 2

Preparation of 3-(R)-amino-1-benzyl-pyrrolidin-2,5-dione acetic acid (1:2)

A solution of 7.80 g of (R)-(1-benzyl-2,5-dioxo-pyrrolidin-3-yl)-carbamic acid benzyl ester (93% (R)-isomer) in 160 ml of acetic acid was treated with 0.78 g of 10% Pd/C (commercially available from Degussa; 1835) and hydrogenated at 30° C. for 20 min whereupon TLC and HPLC indicated completion of the reaction. The reaction mixture was filtered, evaporated and the residue crystallized from EtOAc and n-hexane to give 5.80 g (78%) of 3-(R)-amino-1-benzyl-pyrrolidin-2,5-dione acetic acid (1:2) as white crystals; HPLC (100%): HP 1050, nucleosil 100-5 C18 column, CH₃CN, H₂O, TFA system buffered with TBAHS; GC (99.8% as free amine): J and W, DB-1, 15 m×0.32 mm, carrier gas He, program: 50-320° C. (5° C./min); injector temp. 250° C.; FID: 320° C.; 91% (R)-isomer, analyzed as the corresponding trifluoroacetamide by GC (BGB-177): 15 m×0.25 mm, carrier gas: He; program: 150° C.-200° C. at 1° C./min; injector temp. 210° C.; FID: 220° C.; NMR (CDCl₃, 400 MHz; 1.6 eq AcOH) 7.32 (m, 5H, H-ar), 5.64 (bs, 4H, NH), 4.65 (s, 2H, PhCH₂O, 3.92 (dd, J=5.4 and 7.8, 1H, NCH), 3.05 (dd, J=7.8 and 18, COCH₂, 1H), 2.50 (dd, J=18 and 5.4, COCH₂, 1H), 2.08 (s,2×CH₃CO₂, 6H).

EXAMPLE 3

Preparation of (R)-1-(phenylmethyl)-3-pyrrolidinamine

A solution of 10.87 g of 3-(R)-amino-1-benzyl-pyrrolidine-2,5-dione acetic acid (1:2) in 100 ml of $H_2O$ was treated with 100 ml of $CH_2Cl_2$ followed by 67.60 ml of 1 N NaOH at rt to pH 8.0. After saturation with NaCl, the mixture was extracted seven times with 100 ml of $CH_2Cl_2$, dried over $MgSO_4$ and evaporated at 35° C./10 mbar to give 6.32 g (97%) of the NMR clean free base as a pale yellow solid. NMR ($CDCl_3$, 250 MHz): 7.30 (m, 5H, H-ar), 4.64 (s, 2H, $PhCH_2$), 3.88 (dd, J=5 and 7.5, 1H, NCH), 3.04 (dd, J=7.5 and 17.5, 1H, $COCH_2$), 2.43 (dd, J=5 and 17.5, 1H, $COCH_2$).

5.90 g of this yellow oil was treated at 0° C. over 20 min with 33 ml of a 3.5 M solution of Vitride® in toluene and the resultant yellow-orange solution was warmed to 80° C. for 30 min (MS indicated completion of the reaction), cooled to 0° C. and treated with 80 ml of 1 N NaOH solution. The phases were separated and the aqueous phase extracted with two further portions of 15ml toluene. The combined organic phases were washed with 76 ml 1N NaOH, 70 ml brine, dried and evaporated to give 4.42 g (87%) of (R)-1-(phenylmethyl)-3-pyrrolidinamine, as a light brown oil. GC: (97%, J and W, DB-1, conditions as described for example 2; 93% (R)-isomer, analyzed as the corresponding trifluoroacetamide by GC: (BGB-177), conditions as described for example 2; MS (Ion Spray): 177.1 (M+H$^+$); 1H-NMR ($CDCl_3$, 250 MHz): 7.28 (m, 5H, H-ar), 3.63 and 3.56 (2×d, J=12.5, 2H, $PhCH_2N$), 2.69 (m, 2H, $NCH_2CHNH_2$ and $NCH_2CH_2CHNH_2$), 2.44 (m, 1H, $NCH_2CH_2CHNH_2$), 2.24 (dd, J=4.5 and 9.5, 1H, $NCH_2CHNH_2$), 2.15 (m, 1H, $NCH_2CH_2CHNH_2$), 1.45 (bm, 3H, $NH_2$ and $NCH_2CH_2CHNH_2$); IR (Film): (NH) 3357 (m), (NCH) 2789 (s).

EXAMPLE 4

Preparation of (R)-(1'-benzyl-3-bromo-[1,3']bipyrrolidinyl-2-one)

A solution of 5.0 g of (R)-1-(phenylmethyl)-3-pyrrolidinamine in 50.0 ml $CH_3CN$ was treated at rt with 2.72 g of $Na_3PO_4$. The resulting fine light yellow suspension was cooled to 0° C. and treated with a solution of 10.07 g of 2,4-dibromobutyrylbromide (prepared according to Marinelli, E. R.; Arunachalam, T.; Diamantidis, G.; Emswiler, J.; Fan, H.; Neubeck, R.; Pillai, K. M. R.; Wagler, T. R.; Chen, C.-K.; et al. Tetrahedron (1996), 52(34), 11177-11214) in 5.0 ml of $CH_3CN$ over 20 min. After 30 min the very fine suspension was filtered and concentrated to a volume of 30 ml, and then treated with 130.1 ml of 0.497 M NaOH solution at room temperature. The resultant turbid orange solution was stirred for 2 h, concentrated and the resultant aqueous phase extracted with three portions of 50 ml of TBME. The combined organic phases were washed with $H_2O$ until neutral, dried over $MgSO_4$ and concentrated to give 5.79 g (63%) of (R)-(1'-benzyl-3-bromo-[1,3']bipyrrolidinyl-2-one) as yellow waxy crystals.

The fine suspension from above was triturated with 100 ml $CH_3CN$, filtered, concentrated to a volume of 40 ml and treated with 50 ml of 0.497 m NaOH, then stirred at rt for 1 h. The $CH_3CN$ was distilled away and the resultant aqueous phase worked up as above to give a further 2.57 g (28%) of product. The total yield 8.36 g (91%). $^1$H-NMR ($CDCl_3$, 400 MHz, 14:1 mixture of diastereomers) 7.32 (m, 5H, H-ar), 4.65 (m, 1H, NCH), 4.39 (dd, 1H, CHBr), 3.60 (2d, 2H, $PhCH_2N$), 3.52 (m, 2H, $CONCH_2$),2.92 (ddd, 1H, $PhCH_2NCH_2CH_2$), 2.71 (dd, 1H, $PhCH_2NCH_2CHNCO$), 2.49 (m, 2H, $COCHBrCH_2$ and $PhCH_2NCH_2CH$), 2.25 (m, 3H, $PhCH_2NCH_2CH_2$, $COCHBrCH_2$ and $PhCH_2NCH_2CH_2$), 1.70 (m, 1H, $PhCH_2NCH_2CH_2$).

EXAMPLE 5

Preparation of (R)-(1'-benzyl-2-oxo-[1,3']bipyrrolidinyl-3-yl)-triphenyl-phosphonium; bromide A suspension of 800 mg of 1'-benzyl-3-bromo-[1,3']bipyrrolidinyl-2-one in 1.0 ml toluene was treated with 1.95 g of $Ph_3P$ and stirred at 110° C. for 30 min whereupon TLC indicated the reaction was complete. The brown two phase mixture was diluted with 10 ml EtOAc and the organic phase was extracted with three portions of 10 ml of saturated NaBr solution. The combined aqueous phases were washed three times with 10 ml EtOAc (to remove $Ph_3P$), and then extracted seven times with 15 ml $CH_2Cl_2$, the combined organic phases dried over $MgSO_4$ and concentrated to give 1.13 g (78%) of (R)-(1'-benzyl-2-oxo-[1,3']bipyrrolidinyl-3-yl)-triphenyl-phosphonium bromide as a light brown foam. $^1$H-NMR (250 MHz; $CDCl_3$, ~1:1 mixture of diastereomers): 7.32-8.04 (m, 5H), 7.50-7.82 (m, 10H), 7.19-7.40 (m, 5H), 6.44-6.64 (m, 1H), 4.39-4.50 (m, 1H), 3.10-3.88 (m, 5H), 2.85-3.00 (m, 0.5 H), 2.62-2.80 (m, 1H), 2.32-2.5 (m, 0.5 H), 1.72-2.32 (m, 5H).

EXAMPLE 6

Preparation of (1'-tert-butoxycarbonyl-2-oxo-[1,3']-(R)-bipyrrolidinyl-3-(R,S)-yl)-triphenyl-phosphonium; bromide A solution of the mixture of 880 mg of (R)-(1'-benzyl-2-oxo-[1,3']bipyrrolidinyl-3-yl)-triphenyl-phosphonium bromide and 820 mg of di-tert.-butyl-dicarbonate (commercially available from Fluka) in 5.5 ml MeOH was treated with 880 mg of 10% Pd/C (commercially available from Degussa; 1835) and hydrogenated at 60° C. for 3 d and then filtered and evaporated to give 627 mg (70%) of (1'-tert-butoxycarbonyl-2-oxo-[1,3']-(R)-bipyrrolidinyl-3-(R,S)-yl)-triphenyl-phosphonium; bromide as a beige foam. $^1$H-NMR ($CDCl_3$, 250 MHz; mixture of diastereomers and rotamers): 7.82-8.01 (m, 5H), 7.55-7.81 (m, 10H), 6.71-6.88 (m, 1H), 4.22-4.51 (m, 1H), 3.70-3.91 (m, 1H), 3.35-3.50 (m, 1H), 2.61-3.32 (m, 4H), 1.90-2.20 (m, 2H), 1.64-1.80 (m, 2H), 1.44 (s, 9H).

The invention claimed is:
1. The compound of formula IIIa (R)-(1'-benzyl-3-bromo-[1,3']bipyrrolidinyl-2-one).

* * * * *